(12) United States Patent
Collier et al.

(10) Patent No.: US 7,001,472 B2
(45) Date of Patent: Feb. 21, 2006

(54) METHOD OF SELECTIVELY ANNEALING A NEEDLE

(75) Inventors: John Collier, Franklin Lakes, NJ (US); Leon K. Stungurys, Roanoke, VA (US)

(73) Assignee: Ethicon, Inc., Somerville, NJ (US)

( * ) Notice: Subject to any disclaimer, the term of this patent is extended or adjusted under 35 U.S.C. 154(b) by 254 days.

(21) Appl. No.: 09/978,218

(22) Filed: Oct. 15, 2001

(65) Prior Publication Data

US 2004/0122472 A1 Jun. 24, 2004

(51) Int. Cl.
*C21D 1/04* (2006.01)

(52) U.S. Cl. ............... 148/559; 148/DIG. 3; 606/224
(58) Field of Classification Search ........ 606/139–150, 606/222–233; 29/402.19; 163/1–7; 430/120, 430/209; 148/520, 526, 566–976, DIG. 3, 148/DIG. 4; 266/249, 254, 262
See application file for complete search history.

(56) References Cited

U.S. PATENT DOCUMENTS

| 3,753,412 A | | 8/1973 | Shepard et al. |
| 4,513,747 A | | 4/1985 | Smith |
| 4,524,771 A | | 6/1985 | McGregor et al. |
| 5,701,656 A | * | 12/1997 | Smith et al. ............ 29/558 |
| 5,797,961 A | | 8/1998 | Smith et al. |
| 5,968,394 A | * | 10/1999 | Schob .................... 219/497 |
| 6,018,860 A | * | 2/2000 | Smith et al. ............ 29/558 |

* cited by examiner

*Primary Examiner*—Glenn K. Dawson

(57) ABSTRACT

An improved method of selectively annealing a needle and the needle prepared by the improved method is disclosed. A curved needle is positioned adjacent a flat electromagnetic induction coil. The curved body of the needle is positioned in a plane parallel with the coil plane of the flat induction coil. A current is delivered through the coil to selectively heat and consequently selectively anneal a portion of the needle. The improved method enables the selective annealing of curved needles, and is especially useful for the manufacture of surgical needles.

3 Claims, 4 Drawing Sheets

METHOD OF SELECTIVELY ANNEALING A NEEDLE

BACKGROUND OF THE INVENTION

This invention relates to an improved method of selectively annealing a needle. More specifically, it relates to an improvement in the method of positioning a needle in close proximity with an electromagnetic induction coil and passing current through the coil to selectively anneal a portion of the needle.

U.S. Pat. No. 3,753,412 describes a method of selectively hardening needles. A straight felting needle is positioned in a fixture which is connected to a high-frequency current. An electromagnetic coil is wound about the fixture. The turns of the coil have various diameters and spacings relative to each other. When current is applied to the coil, the needle is heated. The amount of heat applied to a specific section of the needle depends on the diameter and spacings of the coils at that section. Consequently, the needle is selectively hardened.

Unfortunately, the method described in the '412 patent requires the use of a wound coil and the placement of the straight felting needle within the center of the winding. While this method is adequate for a straight needle, it is not practical for a curved needle because of the inability to position a curved needle within the center of the winding of the coil.

The ability to selectively anneal or harden a curved needle is important, especially for the manufacture of curved surgical needles. Curved surgical needles are described in U.S. Pat. Nos. 5,797,961, 4,524,771 and 4,513,747.

A surgical needle is typically attached to a suture during the manufacturing process. Annealing of the needles is generally undertaken for a variety of reasons, one being to facilitate the attachment of the suture to the needle. Typically, the needles are annealed at the portion of the needle commonly referred to as the barrel or channel to soften that portion of the needle to facilitate its attachment to the suture. Maximum softening is often chosen to better control the process. This is necessary due to the difficulty of controlling conventional processes, such as flame annealing or resistance annealing. Flame Annealing is a method of heating a metallic part to a desired temperature for a given amount of time using a flame, in order to reduce the material's strength and improve its ductility. Resistance Annealing is a method of heating a metallic object by applying an electric current through the part, or a region of the part to reduce the material's strength and improve its ductility. Selective annealing, as described in the '412 patent, while often desired, simply cannot be obtained with acceptable certainty for curved needles. As a result, there currently exists an inability to selectively control the portion of the needle which is subjected to the annealing process. This is critical for a surgical needle, since a surgeon expects the finish needle to have consistent strength in the point and body portion of the needle. A precisely selected annealing zone will make it more possible to provide needles which have the requisite consistency in their strength.

In view of the need for a method for selectively annealing a curved needle, and in view of the deficiencies with respect to the prior art for selectively annealing needles, what is needed is an improved method for selectively annealing a curved needle. This improved method would be particularly desirable for the manufacture of curved surgical needles.

SUMMARY OF THE INVENTION

The invention is an improved method of selectively annealing a needle. At least a portion of the needle is positioned in close proximity with an electromagnetic induction coil, and current is provided through the coil to selectively heat the portion of the needle.

The improvement in the method comprises providing the needle with a curved body, configuring the coil with a flat configuration defining a coil plane, positioning at least a portion of the needle adjacent to the flat coil wherein the curved body of the needle is positioned parallel to the coil plane, and providing current through the flat coil to selectively heat the portion of the needle.

The invention is also a needle prepared by this improved method.

In contrast to the prior art, the improved method of this invention enables the selective annealing of a portion of a needle which has a curved body. Instead of using a wound coil, a coil with a flat configuration is used, and at least a portion of the needle is positioned adjacent to the coil so that the curved body of the needle is in a parallel relationship with the coil plane of the flat coil. In this manner, a curved needle can be selectively annealed.

While the method of this invention can be used for the manufacture of curved needles for any application, it is especially advantageous for the manufacturer of curved surgical needles. This improved method will facilitate the selective hardening or softening of different portions of the surgical needle, such as the point, body or attachment area. By controlling the relative hardness of one portion of the needle to another, complex needle geometries can be designed to take advantage of the varying degrees of stiffness at different portions of the needle. This will also lead to process improvements because of the increase in process control, leading to increased efficiencies and reduced waste.

DETAILED DESCRIPTION OF THE PREFERRED EMBODIMENT

Figure 1:
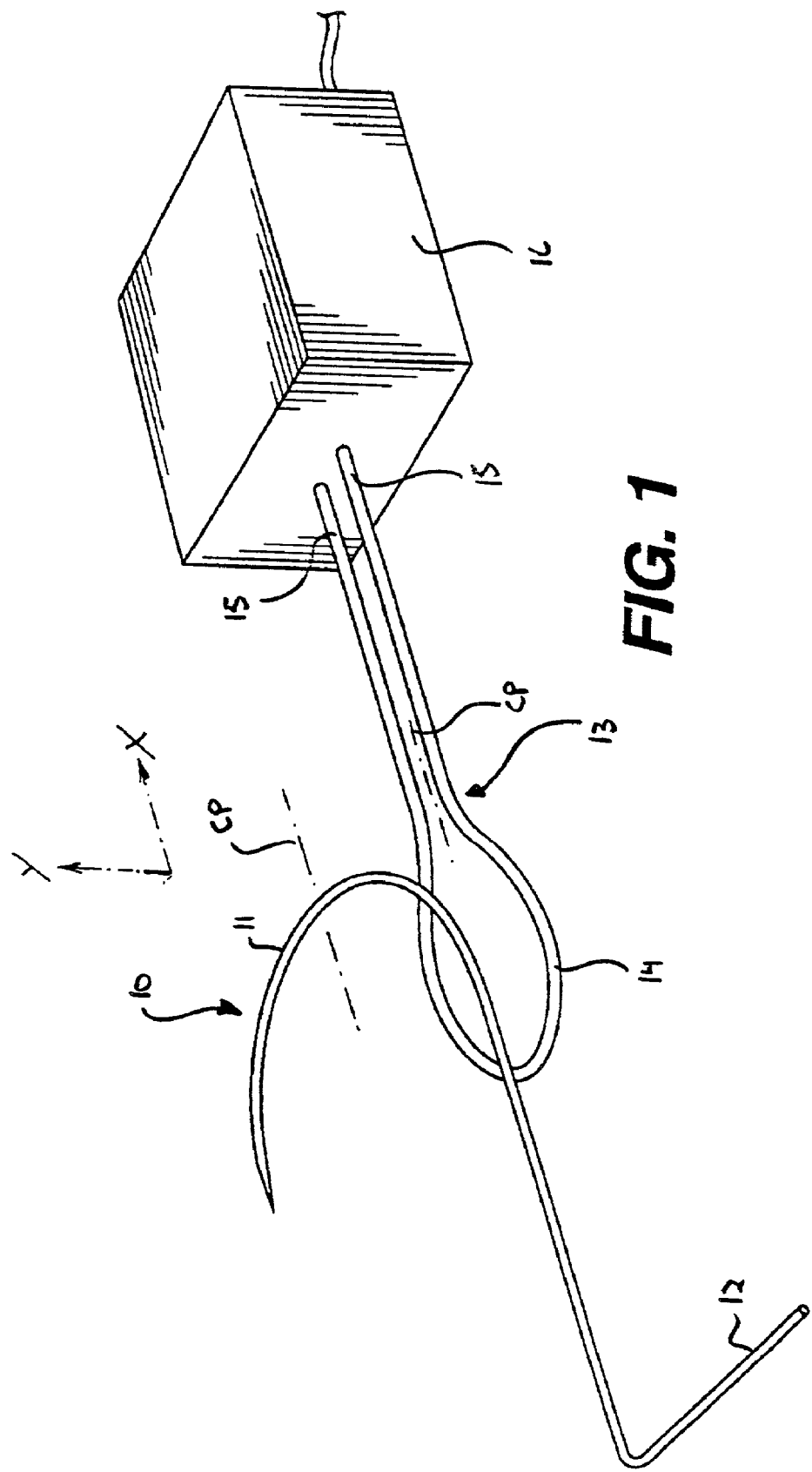
FIG. 1 is a perspective view illustrating the positioning of a curved needle adjacent to an electromagnetic induction coil.
Figure 2:
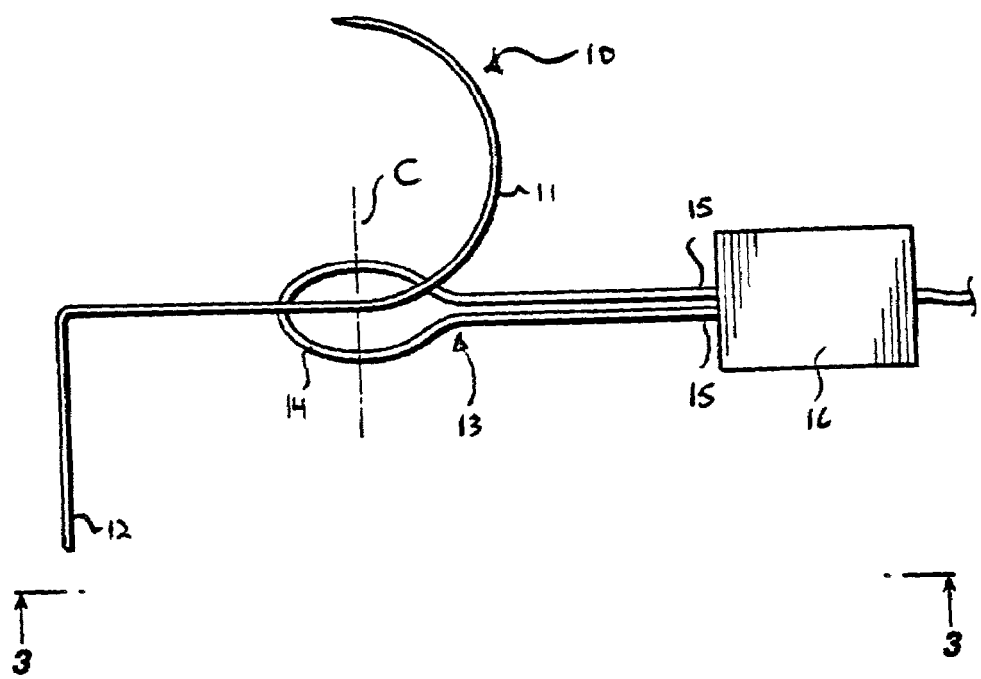
FIG. 2 is a top plan view of FIG. 1.
Figure 3:
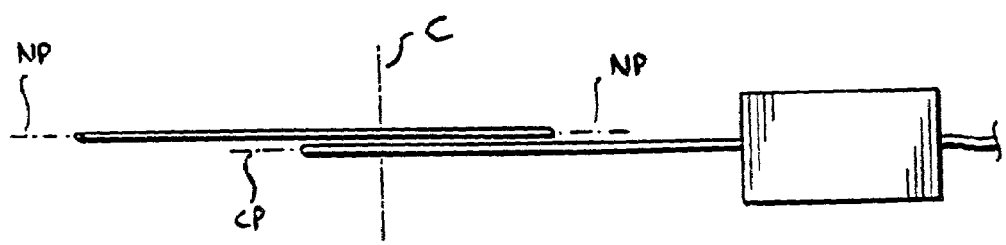
FIG. 3 is a side view as seen along view line 3—3 of FIG. 2.

Referring initially to FIGS. 1–3, a needle 10 which has a curved body 11 is provided. Preferably, the needle has a diameter ranging between about 0.008 to about 0.061 inches. During the manufacturing of the curved needle from wire stock, the needle also includes a tail 12. A portion of the curved needle is positioned adjacent to an electromagnetic induction coil 13.

The induction coil has a flat configuration 14. The coil defines a coil plane designated as "CP" in FIG. 1, and parallel to the "X" axis also depicted in FIG. 1. The curved body 11 of the needle 10 lies in a plane designated as "NP" which is parallel to the coil plane CP of the flat induction coil 13. In this particular embodiment, the needle is positioned relative to the coil to provide the greatest application of heat to that portion of the needle which is subsequently attached to a suture following the selective annealing process. Specifically, this portion is ideally positioned at or near the center of the flat induction coil. As illustrated in FIGS. 2 and 3, the plane designated as "C" is the plane where the end of the needle will be cut from the needle tail. However, the precise positioning of the needle with respect to the coil will depend on numerous factors, including the specific design parameters of the coil and the targeted design parameters for the finished needle. For example, instead of a single coil as illustrated in the figures, a multi-coiled induction coil can be used where each individual coil wraps around adjacent turns within the same plane (not shown in the figures). In an alternative configuration the coils may be wrapped perpendicular to the plane of the coil. In this embodiment the needle may be placed adjacent to the coil, or a space can be provided between adjacent coils, and the needle can be positioned adjacent the coil by passing the needle between the coil space.

The terminals 15 of the inductive coil are connected to a power supply 16 for the delivery of high frequency current to the coil. The requirements for the power supply can be readily determined empirically, and will be based on the induction frequency and power output.

When the needle is positioned relative to the induction coil in the desired manner, high frequency current can then be delivered to the induction coil from the power supply. For the particular embodiment illustrated, to selectively anneal that portion of the needle which is subsequently attached to a suture, the needle portion should be subjected to a temperature sufficient to allow for annealing in less than about 2 seconds, preferably less than about 1 second. The overall length of the anneal zone is desirably less than about 0.25 inches, and preferably less than or equal to about 0.10 inches. Subjecting the needle portion to these annealing conditions will desirably decrease the strength at the annealed zone to less than about 85%, but greater than about 25%, of its initial strength, and preferably between 45% and 75%.

Once heating of the needle for the requisite time at the targeted temperature is accomplished, water can be delivered through the coil for cooling.

Figure 4:
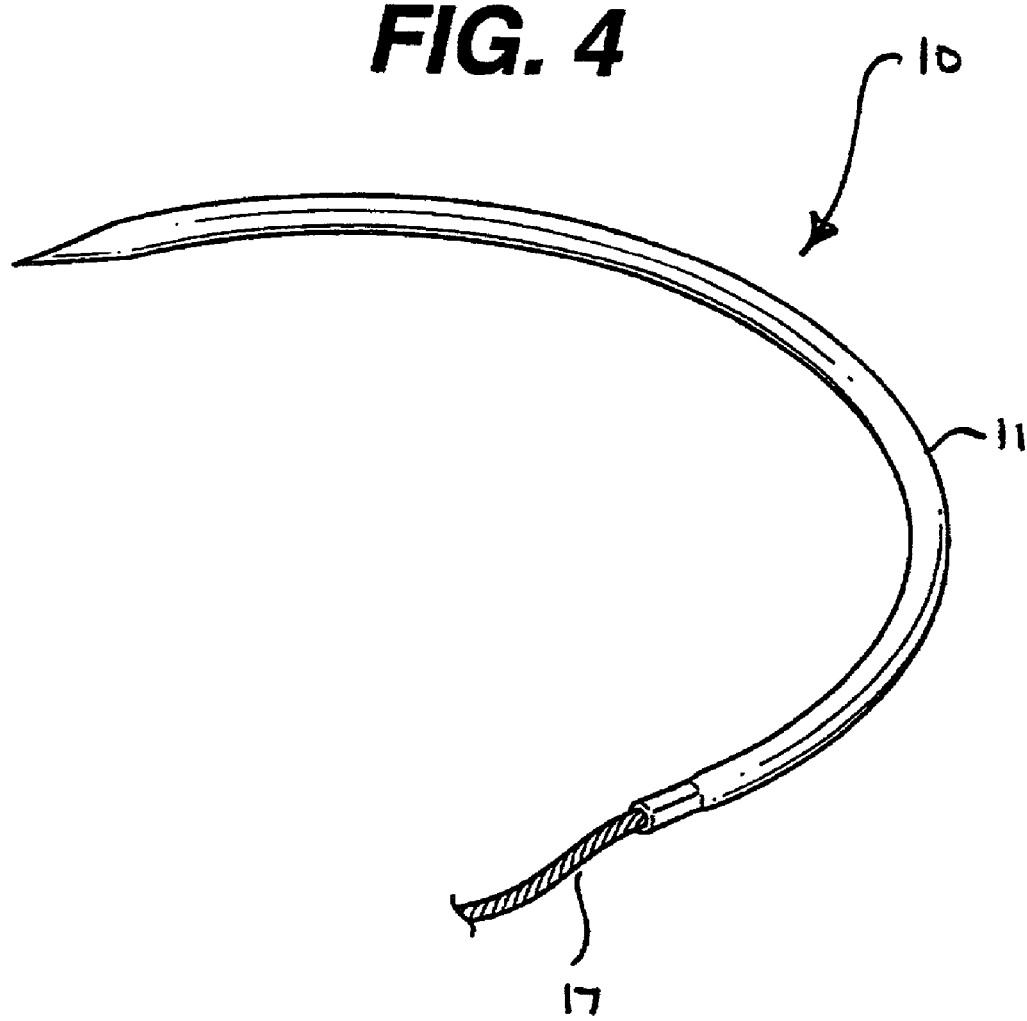
FIG. 4 is a perspective view of a finished needle manufactured in accordance with the improved method of this invention.

Once the needle has been selectively annealed, the remaining steps for manufacturing the finished needle can be performed. Referring specifically to FIGS. 2 and 3, as indicated previously, the tail 12 of the needle can be cut off at the cutting plane designated as "C". Subsequently, the proximal end of the needle can be drilled using conventional drilling methods. Once the needle is drilled, it is subjected to standard finishing and polishing steps. Referring now to FIG. 4, a surgical suture 17 can be attached to the needle through the drill hole at the proximal end of the needle, and subsequently swaged to affix the suture to the needle.

Figure 5:
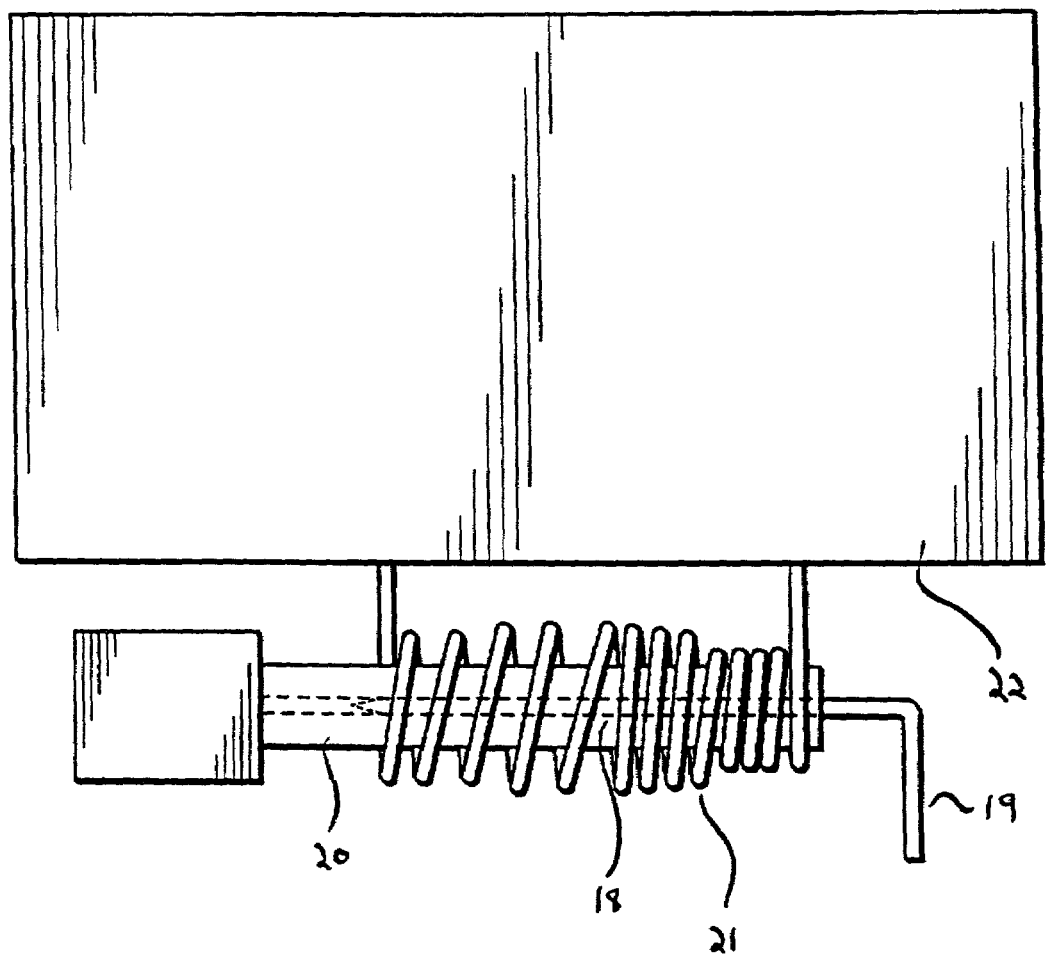
FIG. 5 is a schematic view illustrating the selective hardening methodology of the prior art.

Referring finally to FIG. 5, the prior art methodology of selectively hardening a needle is illustrated. A straight felting needle 18 which includes a tail 19 is provided. The needle is inserted into a fixture 20 for receiving the needle. An electromagnetic induction coil 21 is wound about the fixture. The individual coils differ in diameter and the relative spacing between each of the coils. A power supply 22 delivers current to the coils to selectively harden certain targeted portions of the needle.

Although this invention has been described in connection with its preferred embodiment, numerous additional embodiments are within the spirit and scope of the claimed invention as set forth in the claims which appear below. The preferred embodiment as described in this specification is intended to illustrate but not limit the scope of the invention.

What is claimed is:

1. An improved method of selectively annealing a needle wherein at least a portion of the needle is positioned in close proximity with an electromagnetic induction coil, and current is provided through the coil to selectively heat the portion of the needle; the improvement comprising:
    a) providing the needle with a curved body,
    b) configuring the coil with a flat configuration defining a coil plane,
    c) positioning at least a portion of the needle adjacent to the flat coil wherein the curved body of the needle is positioned parallel to the coil plane, and
    d) providing current through the flat coil to selectively heat the portion of the needle.

2. The improved method of claim 1 wherein the needle is a surgical needle.

3. The improved method of claim 2 wherein the surgical needle has a suture affixed to the needle.

* * * * *